(12) United States Patent
Gall et al.

(10) Patent No.: US 10,623,639 B2
(45) Date of Patent: Apr. 14, 2020

(54) MEDICAL IMAGING APPARATUS (71) Applicant: Siemens Healthcare GmbH, Erlangen (DE)

(72) Inventors: Peter Gall, Uttenreuth (DE); Andreas Greiser, Erlangen (DE); Dominik Paul, Bubenreuth (DE); Daniel Nico Splitthoff, Erlangen (DE); Jens Thoene, Lauf an der Pegnitz (DE); Felix Wolf, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 234 days.

(21) Appl. No.: 15/271,723

(22) Filed: Sep. 21, 2016

(65) Prior Publication Data
US 2017/0085795 A1 Mar. 23, 2017

(30) Foreign Application Priority Data

Sep. 21, 2015 (DE) .................. 10 2015 218 111

(51) Int. Cl.
| | |
|---|---|
| *H04N 5/232* | (2006.01) |
| *G02B 15/14* | (2006.01) |
| *H04N 5/225* | (2006.01) |
| *A61B 5/00* | (2006.01) |
| *A61B 5/055* | (2006.01) |
| *G01R 33/30* | (2006.01) |
| *G01R 33/3815* | (2006.01) |

(Continued)

(52) U.S. Cl.
CPC ....... *H04N 5/23245* (2013.01); *A61B 5/0035* (2013.01); *A61B 5/0077* (2013.01); *A61B 5/055* (2013.01); *G01R 33/307* (2013.01); *G01R 33/385* (2013.01); *G01R 33/3815* (2013.01); *G01R 33/546* (2013.01); *G02B 15/14* (2013.01); *H04N 5/2254* (2013.01); *H04N 5/2257* (2013.01)

(58) Field of Classification Search
CPC ............ H04N 5/23245; H04N 5/2254; H04N 5/2257; A61B 5/0035; A61B 5/0077; A61B 5/055; G01R 33/307; G01R 33/3815; G01R 33/385; G01R 33/546; G02B 15/14

See application file for complete search history.

(56) References Cited

U.S. PATENT DOCUMENTS

| | | | |
|---|---|---|---|
| 2003/0225325 A1 | 12/2003 | Kagermeier et al. | |
| 2004/0258210 A1* | 12/2004 | Ritter .................. | A61B 5/0064 378/198 |

(Continued)

FOREIGN PATENT DOCUMENTS

| | | |
|---|---|---|
| DE | 102013200135 A1 | 7/2014 |
| DE | 102014216718 A1 | 2/2016 |
| WO | WO-2006120605 A1 | 11/2006 |

*Primary Examiner* — Maria E Vazquez Colon
(74) *Attorney, Agent, or Firm* — Schiff Hardin LLP (57) ABSTRACT

A medical imaging apparatus has a data acquisition scanner having a patient receiving zone at least partially enclosed by the scanner, and at least one acquisition unit equipped with a camera to acquire positional data. The at least one acquisition unit has a first imaging optics system and at least one second imaging optics system that differs from the first imaging optics system with regard to at least one optical property or attribute that affects the acquisition of the positional data.

18 Claims, 3 Drawing Sheets

(51) Int. Cl.
*G01R 33/385* (2006.01)
*G01R 33/54* (2006.01)

(56) References Cited

U.S. PATENT DOCUMENTS

| | | | |
|---|---|---|---|
| 2010/0059679 A1* | 3/2010 | Albrecht | A61B 5/0555 |
| | | | 250/338.1 |
| 2013/0076931 A1* | 3/2013 | Border | G02B 27/0075 |
| | | | 348/222.1 |
| 2016/0286120 A1* | 9/2016 | Kuo | H04N 5/23245 |
| 2017/0112416 A1* | 4/2017 | Hao | A61B 6/04 |

\* cited by examiner

MEDICAL IMAGING APPARATUS

BACKGROUND OF THE INVENTION

Field of the Invention

The present invention concerns a medical imaging apparatus having a data acquisition scanner with a patient receiving zone at least partially enclosed by the scanner, and at least one positional data acquisition unit equipped with a camera.

Description of the Prior Art

An acquisition unit is required in order to acquire positional data of a patient prior to and/or during a medical imaging examination by operation of a medical imaging apparatus, for example a magnetic resonance apparatus. Typically, acquisition units of this type have a camera. However, conventional cameras image only a limited area at a high resolution, or a large area at a low resolution.

In known medical imaging systems, a number of acquisition units equipped with a number of cameras are required in order to obtain both positional data of a limited area at a high resolution and positional data of a large area at a low resolution. However, systems of this type require a particularly large amount of installation space, which is disadvantageous particularly when such a system is used inside a patient receiving zone of a magnetic resonance apparatus, and can lead to restrictions in terms of space available for the patient.

SUMMARY OF THE INVENTION

An object of the present invention is to provide a space-saving acquisition unit that enables positional data relating to different areas and/or having different image properties to be acquired in a simple manner.

The invention is based on a medical imaging apparatus having a data acquisition scanner, a patient receiving zone at least partially enclosed by the detector unit, and at least one acquisition unit equipped with a camera to acquire positional data.

In accordance with the invention, the at least one acquisition unit has a first imaging optics system and at least one second imaging optics system that differs from the first imaging optics system with regard to at least one optical property or attribute that affects the acquisition of the positional data.

As used herein, an imaging optics system is a component that may include an optical imaging element or two or more optical imaging elements, such as an objective lens, for example, and/or an optical lens and/or an optical diaphragm and/or an optical filter and/or a mirror and/or an optical diffraction grating, etc. The imaging optics system preferably images a region of the patient receiving zone in order to capture that region with the camera at a resolution predefined by the imaging optics system. In this arrangement, the first imaging optics system and the at least one second imaging optics system are assigned to the one camera, in particular the only camera, of the at least one acquisition unit. Accordingly, at least two imaging optics systems are available for a single camera. Positional data of an examination subject located inside the patient receiving zone, in particular a patient, are acquired by the camera.

As used herein, positional data are positional data relating to the patient, wherein the patient may already be positioned on a patient support of the medical imaging apparatus in preparation for the acquisition of the positional data. For example, the patient can already be positioned in an examination position on the patient support apparatus, particularly advantageously inside the patient receiving zone. Positional data of the patient are preferably acquired during a medical imaging examination by the acquisition unit so that a movement and/or a change of position of the patient during the medical imaging examination can be detected and/or monitored by use of the acquired positional data.

The medical imaging apparatus can be formed by any medical imaging apparatuses considered reasonable to those skilled in the art, such as a computed tomography apparatus, a PET apparatus (positron emission tomography apparatus), etc. Particularly advantageously, however, the present invention is a magnetic resonance apparatus, since in this case movements of the patient during a magnetic resonance examination are particularly undesirable. Due to the relatively long duration of a magnetic resonance examination, it is extremely difficult for patients to remain motionless as much as possible during the entire magnetic resonance examination. With the present invention it is possible in this case to detect and/or monitor a movement and/or a change of position of the patient during the medical imaging examination on the basis of the acquired positional data.

Furthermore, this embodiment of the invention provides a particularly compact and space-saving acquisition unit, which preferably not only enables patient-related positional data having different properties, in particular a different resolution of the different positional data, to be acquired, but also provides positional data covering different fields of view.

In an embodiment, the at least one acquisition unit is arranged inside the patient receiving zone. With this arrangement, it is possible to achieve an advantageous acquisition of positional data of the patient and consequently to detect a movement and/or a change of position of at least one body region to be examined of the patient during the medical imaging examination. The positional data in this embodiment are acquired such that the field of view of the first imaging optics system and/or of the second imaging optics system can be targeted directly onto the body region to be examined of the patient and/or onto an isocenter region of the patient receiving zone of the medical imaging apparatus. In this context, "inside the patient receiving zone" means that the acquisition unit is arranged on a housing and/or wall at least partially enclosing the patient receiving zone and/or is integrated in that housing and/or wall.

In another embodiment of the invention, the first imaging optics system and the at least one second imaging optics system are designed differently in terms of at least one imaging parameter. This allows positional data having different properties and/or positional data of different regions to be acquired with only a single acquisition unit, in particular a single camera of the acquisition unit. The different positional data can be acquired at least partially simultaneously by the one acquisition unit, in particular the single camera of the acquisition unit.

The positional data can be acquired at a first resolution by the first imaging optics system, and positional data can be acquired at a second resolution by the at least one second imaging optics system, the first resolution being higher than the second resolution. Thus, positional data having different resolutions, in particular spatial resolutions, for different monitoring regions and/or fields of view can be made available during the medical imaging examination for the purpose of monitoring and/or supervising the patient. For example, positional data of a body region to be examined of the patient can be provided at a high spatial resolution and positional data of further body regions of the patient can be provided at a lower spatial resolution. A movement of the patient, in particular of the body region to be examined of the patient, can be monitored and/or detected accurately on the basis of the first positional data. Ancillary units, for example an arrangement of local radiofrequency antenna units on the patient, can be detected and/or identified, and/or positional information relating to further body regions of the patient obtained, by the second positional data.

In this context, a resolution means particular a spatial resolution of the positional data, the positional data at the higher spatial resolution containing more accurate spatial information than the positional data at the lower spatial resolution.

In a further embodiment of the invention, the first imaging optics system spans a first field of view and the at least one second imaging optics system spans a second field of view, wherein the first field of view and the second field of view cover at least partially different regions inside the patient receiving zone. This enables positional data of different regions inside the patient receiving zone to be provided. The acquired positional data of the different regions have different optical properties. For example, the different regions can be captured at different spatial resolutions and/or image precisions.

Particularly advantageously, the first imaging optics system has a first field of view that covers a central region of the patient receiving zone. The central region of the patient receiving zone preferably includes the region of an isocenter of the medical imaging apparatus in which the body region to be examined of the patient is arranged for the purpose of the medical imaging examination, so that positional data of said region can be acquired at a particularly high resolution. Also preferably, the at least one second imaging optics system in this case has a second field of view that covers a region inside the patient receiving zone which is outside of the aforementioned central region (the isocenter region) of the patient receiving zone.

A time-saving and rapid acquisition of different positional data, in particular of positional data from different regions inside the patient receiving zone, can be achieved when the first imaging optics system and the at least one second imaging optics system is used simultaneously for the acquisition of different sets of positional data. In this way, not only can positional data be acquired by the first imaging optics system, but also, simultaneously and/or in parallel, positional data are acquired by the second imaging optics system.

In a further embodiment of the invention, the first imaging optics system is mounted in a fixed arrangement on the camera. In this case the first imaging optics system is preferably arranged in a static and/or motionless manner on the camera, in particular on a lens surface of the camera and/or an image acquisition aperture of the camera. This enables first positional data to be acquired by the first imaging optics system independently of the acquisition of positional data by the second imaging optics system. In this case the first imaging optics system is preferably arranged in a central field of view of the camera, the central field of view preferably imaging and/or capturing a central region of the patient receiving zone of the medical imaging apparatus.

Furthermore, the at least one second imaging optics system can also be mounted in a fixed arrangement on the camera. In this case the at least one second imaging optics system is preferably arranged in a static and/or motionless manner on the camera, in particular on a lens surface of the camera and/or an image acquisition aperture of the camera. This enables second positional data to be acquired by the at least one second imaging optics system independently of the acquisition of positional data by the first imaging optics system. In this case the at least one second imaging optics system is preferably arranged in a peripheral region of the field of view of the camera.

In an embodiment having a fixed arrangement of the first imaging optics system and a fixed arrangement of the at least one second imaging optics system, these two imaging optics systems can be adjacent to one another inside the field of view and/or image acquisition aperture and/or a lens surface of the camera, such that a simultaneous and/or parallel acquisition of positional data can be accomplished by the first imaging optics system and the at least one second imaging optics system.

In another embodiment, the first imaging optics system and the at least one second imaging optics system are mounted in a movable arrangement on the camera. The first imaging optics system and the at least one second imaging optics system can be arranged movably on a lens surface and/or an image acquisition aperture and/or a field of view of the camera. This allows the respective imaging optics system to be moved into the field of view of the camera as a function of an application of the camera. In addition, a complete field of view of the camera can be utilized for the respective selected imaging optics system for the acquisition of positional data. Preferably, the displacement is achieved by a guidance device, in particular a mechanical guidance device. The guidance device can have a circular plate on which the individual imaging optics systems are arranged, and the displacement can be effected by means of a rotary movement of the circular plate. In addition, the guidance device may have a plate that executes a translational movement and/or a linear movement, and the individual imaging optics systems can be arranged in succession on the plate.

Furthermore, the at least one second imaging optics system can have a portion that is formed by the first imaging optics system and another portion of the at least one second imaging optics system can be arranged movably on the first imaging optics system. This makes it particularly easy to switch between the individual imaging optics systems for the respective acquisition of different positional data sets. In addition, a complete field of view and/or a complete lens surface and/or a complete image acquisition aperture of the camera can be used for the respective selected imaging optics system for the purpose of acquiring the positional data. In this case the subsection of the at least one second imaging optics system can likewise include a further imaging optics system. The at least one second imaging optics system in this case comprises the further imaging optics system and the first imaging optics system, which are arranged one after the other along an acquisition direction of the at least one second imaging optics system. In this case the first imaging optics system can be mounted in a fixed arrangement on the camera and only the subsection, in particular having the further imaging optics system, can be arranged so as to movable.

In another embodiment, the first imaging optics system and the at least one second imaging optics system are designed so as to be at least partially integrally formed as a single piece with one another. This enables a particularly compact and space-saving acquisition unit to be provided for the purpose of acquiring positional data during a medical imaging examination.

In a further embodiment of the invention, the first imaging optics system and the at least one second imaging optics system have two or more imaging elements and a switchover between the first imaging optics system and the at least one second imaging optics system involves a variation of a distance between the two or more imaging elements. This enables a simple and rapid switchover to be effected between the first imaging optics system and the at least one second imaging optics system. In addition, the first imaging optics system can be integrated together with the at least one second imaging optics system in a particularly compact and space-saving configuration inside the acquisition unit.

In another embodiment, the acquisition unit has a zoom lens and the first imaging optics system has a first imaging setting of the zoom lens and the at least one second imaging optics system has a second imaging setting of the zoom lens. The first imaging setting of the zoom lens is different from the second imaging setting of the zoom lens. This enables a simple and rapid switchover between the first imaging optics system and the at least one second imaging optics system. In addition, the first imaging optics system can be integrated together with the at least one second imaging optics system in a particularly compact and space-saving configuration inside the acquisition unit. A zoom lens in this context means an objective lens that has individual imaging elements and/or lens elements, with a displacement of the imaging elements and/or of the lens elements relative to one another producing a change in the focal length of the objective lens.

In a further embodiment of the invention, the acquisition unit can have an adjustment unit configured for adjusting a setting of the first imaging optics system or of the at least one second imaging optics system. This allows a simple and convenient adjustment of the first imaging optics system or the second imaging optics system. In addition, a rapid switchover between the first imaging optics system and the at least one second imaging optics system can be effected so that, as a result, the acquisition unit can be employed for detecting a trigger movement, such as a respiratory motion, for operating the medical imaging examination.

DESCRIPTION OF THE PREFERRED EMBODIMENTS

Figure 1:
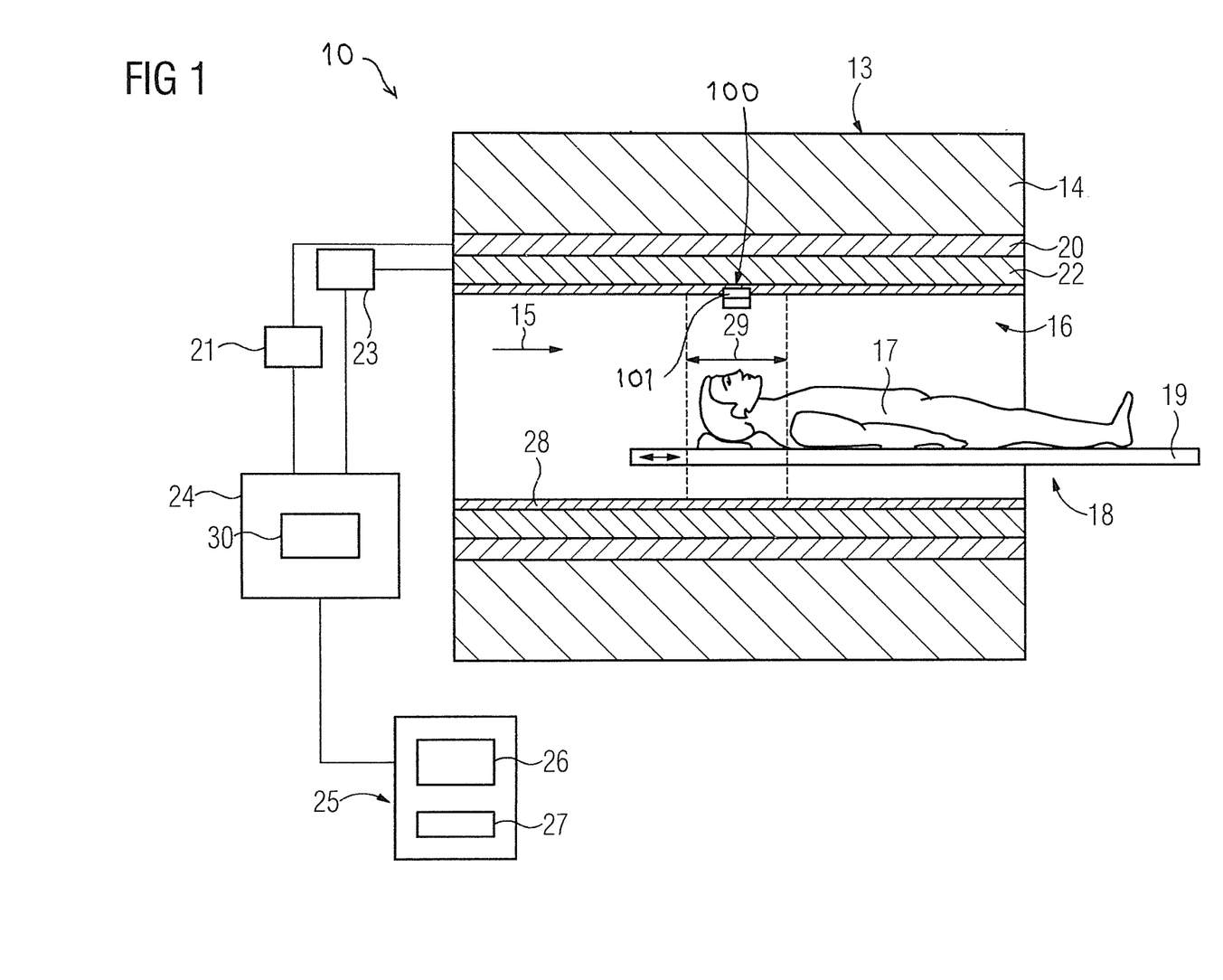
FIG. 1 shows an inventive medical imaging apparatus having an acquisition unit, in a schematic illustration.

A medical imaging apparatus 10 is depicted schematically in FIG. 1. In that exemplary embodiment, the medical imaging apparatus 10 is formed by a magnetic resonance apparatus, the present invention being explained on the basis of the magnetic resonance apparatus as an example. However, the present invention is not limited to an embodiment of the medical imaging apparatus 10 in the form of a magnetic resonance apparatus, and further modalities of the medical imaging apparatus 10 are conceivable.

The magnetic resonance apparatus has a magnetic resonance data acquisition scanner 13 having a basic field 14 magnet formed as a superconducting basic magnet for generating a strong and constant basic magnetic field 15. The scanner 13 has a patient receiving zone 16 for accommodating a patient 17. The patient receiving zone 16 in the present exemplary embodiment has a cylinder shape and is cylindrically enclosed by the basic field magnet 14 in a circumferential direction. In principle, however, a different design of the patient receiving zone 16 is conceivable. The patient 17 can be introduced into the patient receiving zone 16 by a patient support 18. For this purpose, the patient support 18 has a patient table 19 that is movable inside the patient receiving zone 16.

The scanner 14 also has a gradient coil arrangement 20 for generating magnetic field gradients that are used for spatial encoding during an imaging session. The gradient coil arrangement 20 is controlled by a gradient controller 21. The scanner 14 also has a radiofrequency (RF) antenna 22 controlled by a radiofrequency antenna controller 23 so as to radiate radiofrequency sequences into an examination space that is substantially formed by the patient receiving zone 16 of the magnetic resonance apparatus 11. The radiofrequency sequences excite certain nuclear spins in the patient 17 so as to give the excited spins a magnetization that deviates from the polarization established by the basic magnetic field 15. As the excited spins relax, they emit magnetic resonance signals that are detected by the RF antenna 22, or by another RF antenna provided for that purpose.

In order to control the basic field magnet 14, the gradient controller 21 and the radiofrequency antenna controller 23, the magnetic resonance apparatus 11 has a system control computer 24. The system control computer 24 is responsible for the centralized control of the magnetic resonance apparatus 11, such as performing a predetermined imaging gradient echo sequence. In addition, the system control computer 24 has an evaluation processor (not separately shown) for evaluating medical image data acquired during the magnetic resonance examination.

The magnetic resonance apparatus 11 furthermore has a user interface 25, which is connected to the system control computer 24. Control information such as e.g. imaging parameters, as well as reconstructed magnetic resonance images, can be displayed on a visualization unit 26, for example on at least one monitor, of the user interface 25 for a member of the medical operating staff. The user interface 25 additionally has an input unit 27 via which information and/or parameters can be entered by the medical operating staff during a measurement procedure.

In order to acquire positional data of in particular the patient 17 during a magnetic resonance examination, the magnetic resonance apparatus 11 has an acquisition unit 100. Different exemplary embodiments of the acquisition unit 100, respectively designated as 200, 300, 400, are depicted in more detail in FIGS. 2 to 5.

Figure 2:
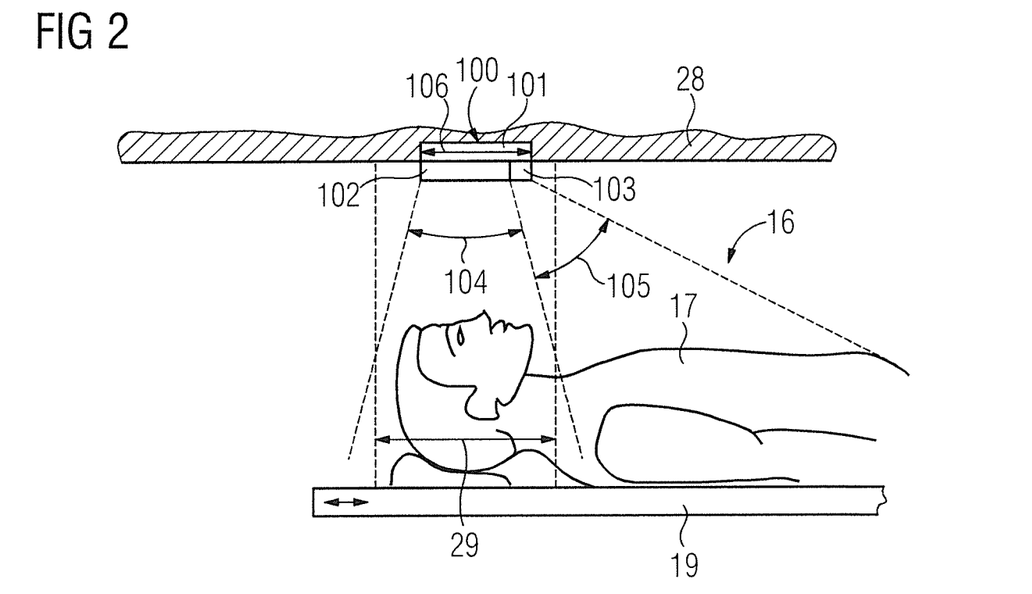
FIG. 2 shows a first exemplary embodiment of the acquisition unit, in a schematic illustration.

FIG. 2 shows a first exemplary embodiment of the acquisition unit 100. The acquisition unit has a single camera 101 for acquiring the positional data. In the present exemplary embodiment, the magnetic resonance apparatus 11 has a single acquisition unit 100. In an alternative embodiment of the invention, the magnetic resonance apparatus 11 can have two or more acquisition units 100.

The acquisition unit 100, in particular the camera 101, is arranged inside the patient receiving zone 16, the acquisition unit 100, in particular the camera 101, in this case being arranged on a wall 28 of the magnetic resonance apparatus 11 enclosing the patient receiving zone 16. In the present exemplary embodiment, the acquisition unit 100, in particular the camera 101, is arranged inside a central region 29 of the patient receiving zone 16.

The acquisition unit 100 has a first imaging optics system 102 and a second imaging optics system 103. The first imaging optics system 102 and the second imaging optics system 103 preferably each image a region of the patient receiving zone 16 in order to capture that region by means of the camera 101 at a resolution predefined by the imaging optics system 102, 103. In principle the acquisition unit 100 can also have more than two imaging optics systems 102, 103. The first imaging optics system 102 and/or the second imaging optics system 103 include optical imaging elements, such as an objective lens, and/or an optical lens and/or an optical diaphragm and/or an optical filter and/or a mirror and/or an optical diffraction grating, etc.

The first imaging optics system 102 and the second imaging optics system 103 differ from one another in terms of at least one imaging parameter. In this regard, positional data can be acquired at a first resolution, in particular a first spatial resolution, by the first imaging optics system 102, and positional data can be acquired at a second resolution, in particular a second spatial resolution, by the second imaging optics system 103. The first resolution is higher than the second resolution. The positional data at the higher spatial resolution thus contain more accurate spatial information than the positional data at the lower spatial resolution. The resolution (spatial resolution) of the first imaging optics system 102 and the resolution (the spatial resolution) of the second imaging optics system 103 are in this case set as permanent and/or unchangeable.

The first imaging optics system 102 covers a first field of view 104 and the second imaging optics system 103 covers a second field of view 105. The first field of view 104 and the second field of view 105 in this embodiment to not coincide, so the first field of view 104 and the second field of view 105 respectively cover at least partially different regions inside the patient receiving zone 16. In the exemplary embodiment, the first field of view 104 covers the central region 29 of the patient receiving zone 16. The central region 29 of the patient receiving zone 16 contains the region of an isocenter of the medical imaging apparatus 10, in particular of the scanner 14. The second field of view 105 covers a region of the patient receiving zone 16 that is contiguous with the central region 29 containing the isocenter region. In this case the second field of view 105 can cover a greater region of the patient receiving zone 16 than the first field of view 104.

In such a way, positional data of a body region to be examined, which is arranged inside the central region 29 of the patient receiving zone 16 and/or inside the isocenter region, can be provided at a high spatial resolution, and positional data relating to further body regions, which are arranged outside of the central region 29 of the patient receiving zone 16 and/or outside of the isocenter region, can be provided at a lower spatial resolution. In the exemplary embodiment, the first field of view 104 and the second field of view 105 are contiguous with one another. In an alternative embodiment of the invention, the first field of view 104 and the second field of view 105 can partially overlap one another.

In this arrangement, the first imaging optics system 102 covers a section of the camera 101, in particular an image acquisition aperture 106 of the camera 101 and/or a lens surface of the camera 101, that is larger than a section of the camera 101, in particular an image acquisition aperture 106 of the camera 101 and/or a lens surface of the camera 110 which is covered by the second imaging optics system 103. Preferably, the section of the camera 101, in particular the image acquisition aperture 106 of the camera 101, which is covered by the first imaging optics system 102 is two times larger than the section of the camera 101, in particular the image acquisition aperture 106 of the camera 101, which is covered by the second imaging optics system 103. Preferably, the section of the camera 101, in particular the image acquisition aperture 106 of the camera 101, which is covered by the first imaging optics system 102 is five times larger than the section of the camera 101, in particular the image acquisition aperture 106 of the camera 101, which is covered by the second imaging optics system 103. Preferably, the section of the camera 101, in particular the image acquisition aperture 106 of the camera 101, which is covered by the first imaging optics system 102 is seven times larger than the section of the camera 101, in particular the image acquisition aperture 106 of the camera 101, which is covered by the second imaging optics system 103. In the present exemplary embodiment, the section of the camera 101, in particular the image acquisition aperture 106 of the camera 101, which is covered by the first imaging optics system 102 is nine times larger than the section of the camera 101, in particular the image acquisition aperture 106 of the camera 101, which is covered by the second imaging optics system 103. In this case the first imaging optics system 102 covers 90% of the image acquisition aperture 106 of the camera 101 and/or of the lens surface of the camera 101, and the second imaging optics system 103 covers 10% of the image acquisition aperture 106 of the camera 101 and/or of the lens surface of the camera 101. Because of their fixed arrangement on the camera 101, the first imaging optics system 102 and the second imaging optics system 103 can also form the lens surface of the camera 101.

In the exemplary embodiment, the first imaging optics system 102 is mounted in a fixed arrangement on the camera 101. The second imaging optics system 103 is also mounted in a fixed arrangement on the camera 101 in the present exemplary embodiment. In this case the first imaging optics system 102 and also the second imaging optics system 103 are arranged in a static and/or motionless manner on the camera 101. The first imaging optics system 102 is mounted in a fixed arrangement on the camera 101 in such a way that the first imaging optics system 102 covers a central field of view of the camera 101. The second imaging optics system 103 is mounted in a fixed arrangement on the camera 101 in such a way that the second imaging optics system 103 covers a peripheral region of the field of view of the camera 101. The first imaging optics system 102 and the second imaging optics system 103 are in this case arranged contiguously with one another and/or adjacent to one another on the camera 101, in particular on the image acquisition aperture 106 of the camera 101.

By virtue of the contiguous arrangement of the first imaging optics system 102 and the second imaging optics system 103 on the camera 101, first positional data and second positional data can advantageously be acquired simultaneously by means of the first imaging optics system 102 and the second imaging optics system 103, respectively.

The acquired positional data are transferred to a positional data evaluation processor 30 that is integrated in the system control computer 24 and is evaluated there. In this case the first positional data at the high spatial resolution is used by the positional data evaluation unit 30 for monitoring the position of the body region to be examined of the patient 17 and/or for monitoring movement of the body region to be examined of the patient 17 during the magnetic resonance examination. For example, a head movement and/or an eye movement of the patient 17 during a head examination can be detected. The second positional data at the low spatial resolution are used by the positional data evaluation processor 30 in order to identify for example further ancillary units, such as further local radiofrequency antenna units that are arranged on the patient 17.

In order to evaluate the acquired first positional data and/or the acquired second positional data, the positional data evaluation processor 30 has software and/or computer programs designed for that purpose.

Figure 3:
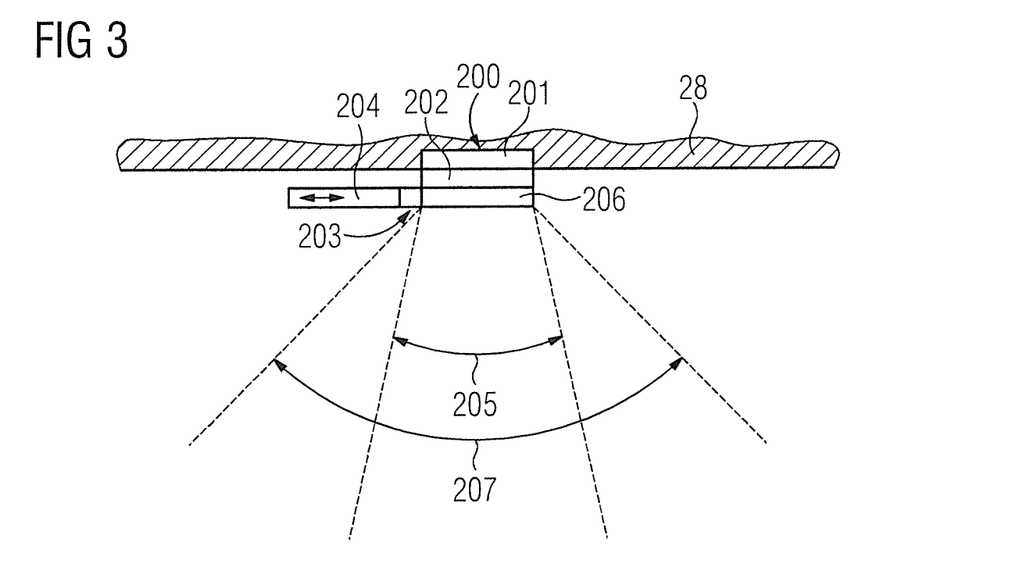
FIG. 3 shows a second exemplary embodiment of the acquisition unit, in a schematic illustration.

FIG. 3 shows an alternative exemplary embodiment of the acquisition unit 200. Components, features and functions remaining substantially the same are labeled consistently with the same reference numerals. The following description limits itself essentially to the differences compared to the exemplary embodiment in FIG. 2, with reference being made to the description of the exemplary embodiment in FIG. 2 in respect of components, features and functions that remain the same.

The acquisition unit 200 in FIG. 3 likewise comprises a single camera 201 having a first imaging optics system 202 and a second imaging optics system 203. In the present exemplary embodiment, the first imaging optics system 202 is mounted in a fixed arrangement on the camera 201. First positional data can be acquired the first imaging optics system 202. The second imaging optics system 203 includes the first imaging optics system 202 and another portion having a further imaging optics system 204. The further imaging optics system 204 is in this case arranged and/or mounted movably on the first imaging optics system 202. The further imaging optics system 204 can accordingly be moved in the direction of a positional radiation from inside the patient receiving zone 16 toward the camera 201 directly in front of the first imaging optics system 202 for the purpose of acquiring second positional data. In this case the further imaging optics system 204 is located directly in a first field of view 205 of the first imaging optics system 202. If only the first imaging optics system is active, the further imaging optics system 204 is arranged outside of the first field of view 205 of the first imaging optics system 202.

In order to displace the further imaging optics system 204, the second imaging optics system 203 has a guidance device 206, in particular a mechanical guidance unit, which is depicted only schematically. The guidance device 206 is in this case arranged on the first imaging optics system 202 of the camera 201. In addition, the guidance device 206 and/or the second imaging optics system 203 can have an adjustment unit (not shown in further detail) which is configured to perform a self-actuating and/or automatic adjustment of the setting of the first imaging optics system 202 and/or of the second imaging optics system 203 and accordingly independently and/or automatically controls a position and/or a movement of the further imaging optics system 204.

The first imaging optics system 202 and the second imaging optics system 203 differ from one another in terms of at least one imaging parameter. In this case, positional data can be acquired at a first resolution, in particular a first spatial resolution, by the first imaging optics system 202, and positional data can be acquired at a second resolution, in particular a second spatial resolution, by the second imaging optics system 203. The first resolution (first spatial resolution) is in this case higher than the second resolution (second spatial resolution). The positional data at the higher spatial resolution contain more accurate spatial information than the positional data at the lower spatial resolution.

The first imaging optics system 202 covers the first field of view 205 and the second imaging optics system 204 covers a second field of view 207. The first field of view 205 and the second field of view 207 are in this case embodied at least partially differently, the first field of view 205 and the second field of view 207 in this case covering at least partially different regions inside the patient receiving zone 16. In this exemplary embodiment, the first field of view 205 covers a central region 29 of the patient receiving zone 16. In the present exemplary embodiment, the second field of view 207 can in this case cover both the first field of view 205 and a region inside the patient receiving zone 16 which is contiguous with the first field of view 205. In such a way, positional data of a body region to be examined which is preferably inside the central region 29 of the patient receiving zone 16 and/or inside the isocenter region can be provided at a high spatial resolution and positional data of further body regions which are arranged outside of the central region 29 of the patient receiving zone 16 and/or outside of the isocenter region can be provided at a lower spatial resolution.

Figure 4:
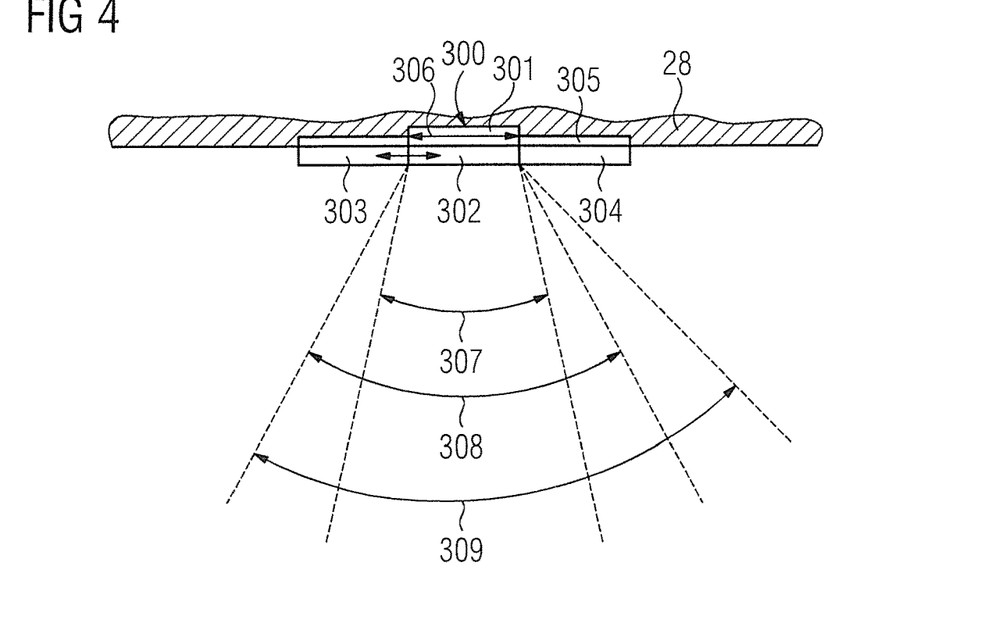
FIG. 4 shows a third exemplary embodiment of the acquisition unit, in a schematic illustration.

FIG. 4 shows an alternative exemplary embodiment of the acquisition unit 300. Components, features and functions remaining substantially the same are labeled consistently with the same reference numerals. The following description limits itself essentially to the differences compared to the exemplary embodiment in FIGS. 2 and 3, with reference being made to the description of the exemplary embodiment in FIGS. 2 and 3 in respect of components, features and functions that remain the same.

The acquisition unit 300 in FIG. 4 likewise has a single camera 301 having a first imaging optics system 302, a second imaging optics system 303 and a third imaging optics system 304. The first imaging optics system 302, the second imaging optics system 303 and the third imaging optics system 304 are in this case movably arranged and/or mounted on the camera 301. In order to displace the first imaging optics system 302, the second imaging optics system 303 and the third imaging optics system 304, the acquisition unit 300 has a guidance unit 305, in particular a mechanical guidance unit.

Depending on application, the corresponding imaging optics system 302, 303, 304 can be moved into a field of view of the camera 301, in particular into an image acquisition aperture 306 of the camera 301, and be arranged there. Each of the three imaging optics systems 302, 303, 304 has a size that corresponds to a size of the image acquisition aperture 306 of the camera 301 such that full use can be made of the camera 301 by means of each of the three imaging optics systems 302, 303, 304. In this configuration, the guidance unit 305 is arranged on the camera 301, in particular on the image acquisition aperture 306 of the camera 301. In addition, the guidance unit 305 and/or the acquisition unit 300 can have an adjustment unit (not shown in further detail) which is configured to perform a self-actuating and/or automatic adjustment of the setting of the first imaging optics system 302 and/or of the second imaging optics system 303 and/or of the third imaging optics system 304.

First positional data can be acquired by the first imaging optics system 302, second positional data can be acquired by the second imaging optics system 303, and third positional data can be acquired by the third imaging optics system 304. The first imaging optics system 302, the second imaging optics system 303 and the third imaging optics system 304 differ from one another in terms of at least one imaging parameter. In this case, positional data can be acquired at a first resolution, in particular a first spatial resolution, by the first imaging optics system 302, positional data can be acquired at a second resolution, in particular a second spatial resolution, by means of the second imaging optics system 303, and positional data can be acquired at a third resolution, in particular a third spatial resolution, by the third imaging optics system 304. The first resolution is in this case higher than the second resolution, and/or higher than the third resolution. The positional data at the higher spatial resolution contain more accurate spatial information than the positional data at the lower spatial resolution.

The first imaging optics system 302 covers a first field of view 307, the second imaging optics system 303 covers a second field of view 308, and the third imaging optics system 304 covers a third field of view 309. The first field of view 307, the second field of view 308 and the third field of view 309 are in this case embodied at least partially differently, the first field of view 307, the second field of view 308 and the third field of view 309 in this case covering at least partially different regions inside the patient receiving zone 16. The first field of view 307 covers a central region 29 of the patient receiving zone 16. In the present exemplary embodiment, the second field of view 308 can in this case cover both the first field of view 307 and a region inside the patient receiving zone 16 which is contiguous with the first field of view 307. In addition, the third field of view 309 can also cover both the first field of view 307 and a region inside the patient receiving zone 16 which is contiguous with the first field of view 307, it being possible for the second field of view 308 and the third field of view 309 to cover different regions of the patient receiving zone 16. In such a way, positional data of a body region to be examined, which is preferably inside the central region 29 of the patient receiving zone 16 and/or inside the isocenter region, can be provided at a high spatial resolution, and positional data of further body regions, which are arranged outside of the central region 29 of the patient receiving zone 16 and/or outside of the isocenter region, can be provided at a lower spatial resolution.

Figure 5:
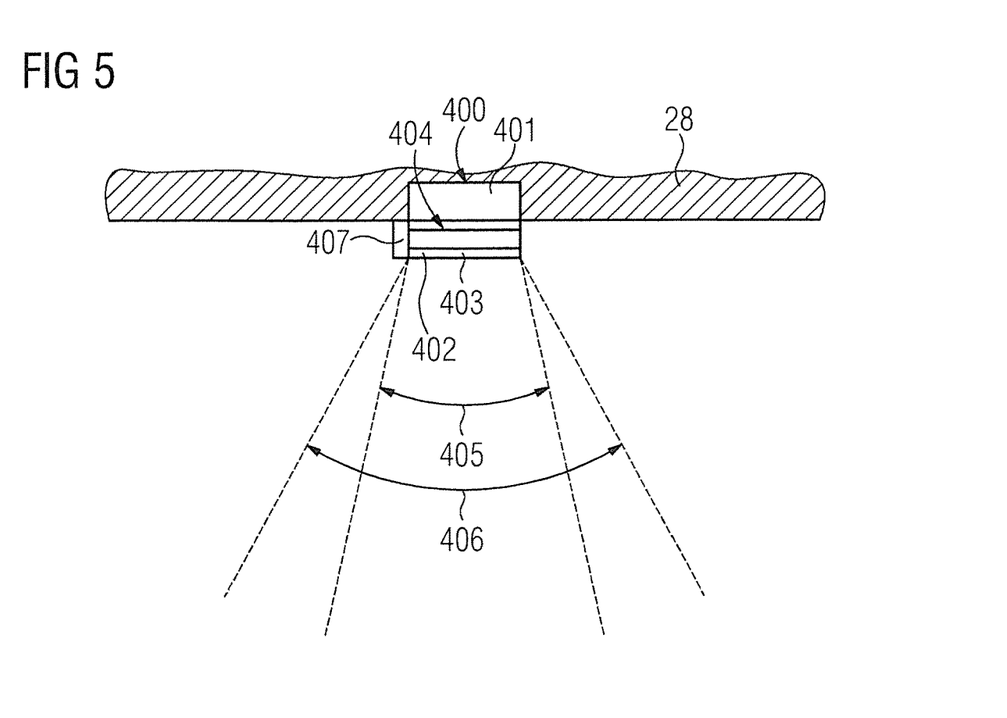
FIG. 5 shows a fourth exemplary embodiment of the acquisition unit, in a schematic illustration.

FIG. 5 shows an alternative exemplary embodiment of the acquisition unit 400. Components, features and functions remaining substantially the same are labeled consistently with the same reference numerals. The following description limits itself essentially to the differences compared to the exemplary embodiment in FIGS. 2 to 4, with reference being made to the description of the exemplary embodiment in FIGS. 2 to 4 in respect of components, features and functions that remain the same.

The acquisition unit 400 in FIG. 5 has a single camera 401 having a first imaging optics system 402 and a second imaging optics system 403. The first imaging optics system 402 and the second imaging optics system 403 are embodied at least partially integrally formed as a single piece with one another. In this case the first imaging optics system 402 and the second imaging optics system 403 have two or more imaging elements, a switchover between the first imaging optics system 402 and the second imaging optics system 403 involving a variation of a distance between the two or more imaging elements. The individual imaging elements are in this case encompassed by a zoom lens 404 of the acquisition unit 400, the first imaging optics system 402 comprising a first imaging setting of the zoom lens 404 and the second imaging optics system 403 comprising a second imaging setting of the zoom lens 404.

First positional data can be acquired by the first imaging optics system 402 and second positional data can be acquired by the second imaging optics system 403. The first imaging optics system 402 and the second imaging optics system 403 differ from one another in terms of at least one imaging parameter. In this case, positional data can be acquired at a first resolution, in particular a first spatial resolution, by the first imaging optics system 402, and positional data can be acquired at a second resolution, in particular a second spatial resolution, by the second imaging optics system 403. The first resolution is in this case higher than the second resolution. The positional data at the higher spatial resolution contain more accurate spatial information than the positional data at the lower spatial resolution.

The first imaging optics system 402 covers a first field of view 405 and the second imaging optics system 403 covers a second field of view 406. The first field of view 405 and the second field of view 406 are in this case embodied at least partially differently, the first field of view 405 and the second field of view 406 in this case covering at least partially different regions inside the patient receiving zone 16. In this exemplary embodiment, the first field of view covers a central region 29 of the patient receiving zone 16. In the present exemplary embodiment, the second field of view 406 can in this case cover both the first field of view 405 and a region inside the patient receiving zone 16 which is contiguous with the first field of view 405. In such a way, positional data of a body region to be examined, which is preferably inside the central region 29 of the patient receiving zone 16 and/or inside the isocenter region, can be provided at a high spatial resolution, and positional data of further body regions, which are outside of the central region 29 of the patient receiving zone 16 and/or outside of the isocenter region, can be provided at a lower spatial resolution.

By a rapid switchover between the first imaging optics system 402 and the second imaging optics system 403, it is possible to capture a large overview region by the second imaging optics system 403 and in addition to acquire positional data for detecting a respiratory motion of the patient 17 during the magnetic resonance examination by the first imaging optics system 402. The rapid switchover can be effected, for example, at a sampling rate of less than 1/s, since this allows an advantageous detection of a respiratory motion of the patient 17.

The switchover is preferably accomplished by an adjustment unit 407 of the acquisition unit 400, in particular of the zoom lens 400, the adjustment unit 407 being configured to perform a self-actuating and/or automatic adjustment of the setting of the first imaging optics system 402, in particular the first imaging setting of the zoom lens 404, and/or of the second imaging optics system 403, in particular the second imaging setting of the zoom lens 404.

Although modifications and changes may be suggested by those skilled in the art, it is the intention of the inventors to embody within the patent warranted hereon all changes and modifications as reasonably and properly come within the scope of their contribution to the art.

We claim as our invention:

1. A medical imaging apparatus comprising:
   a medical image data acquisition scanner having a patient receiving zone at least partially enclosed by said medical image data acquisition scanner;
   at least one positional data acquisition unit equipped with a camera and configured to acquire positional data relevant to the acquisition of said medical image data; and
   said at least one positional data acquisition unit comprising a first imaging optics system and at least one second imaging optics system that differs from said first imaging optics system with regard to at least one imaging property or attribute that affects the acquisition of said positional data,
   wherein each of the first imaging optics system and the second imaging optics system, when operated simultaneously, provide different respective fields of view inside said patient receiving zone to at least partially cover different regions inside the patient receiving zone, and wherein the camera associated with the at least one positional data acquisition unit includes said first imaging optics system and said at least one second imaging optics system, which are integrally formed as a single unitary component.

2. The medical imaging apparatus as claimed in claim 1, wherein said at least one positional data acquisition unit is situated inside said patient receiving zone.

3. The medical imaging apparatus as claimed in claim 1, wherein said first imaging optics system and said second imaging optics system differ from each other with regard to at least one imaging parameter.

4. The medical imaging apparatus as claimed in claim 1, wherein said first imaging optics system is configured to acquire said positional data at a first resolution, and wherein said second imaging optics system is configured to acquire said positional data at a second resolution, said first resolution being higher than said second resolution.

5. The medical imaging apparatus as claimed in claim 1, wherein said first imaging optics system has a first field of view, and wherein said at least one second imaging optics system has a second field of view that does not coincide with said first field of view inside said patient receiving zone.

6. The medical imaging apparatus as claimed in claim 1, wherein said first imaging optics system has a field of view, and wherein said field of view encompasses a central region of said patient receiving zone.

7. The medical imaging apparatus as claimed in claim 1, wherein said at least one positional data acquisition unit is configured to operate said first imaging optics system and said at least one second imaging optics system simultaneously to acquire respectively different sets of said positional data.

8. The medical imaging apparatus as claimed in claim 1, wherein said first imaging optics system is fixedly mounted on said camera.

9. The medical imaging apparatus as claimed in claim 1, wherein said at least one second imaging optics system is fixedly mounted on said camera.

10. The medical imaging apparatus as claimed in claim 1, wherein said first imaging optics system and said at least one second imaging optics system are movably mounted on said camera.

11. The medical imaging apparatus as claimed in claim 1, wherein a portion of said at least one second imaging optics system comprises said first imaging optics system, and another portion of said at least one second imaging optics system is movably mounted on said first imaging optics system.

12. The medical imaging apparatus as claimed in claim 1, wherein said first imaging optics system and said at least one second imaging optics system each have at least two imaging elements, and wherein said at least one positional data acquisition unit is configured to switch between said first imaging optics system and said at least one second imaging optics system by varying a distance between said at least two imaging elements.

13. The medical imaging apparatus as claimed in claim 1, wherein said at least one positional data acquisition unit comprises a zoom lens, and wherein said first imaging optics system comprises a first imaging setting of said zoom lens, and said at least one second imaging optics system comprises a second imaging setting of said zoom lens, said first imaging setting being different from said second imaging setting.

14. The medical imaging apparatus as claimed in claim 13, wherein said at least one positional data acquisition unit is configured to adjust the setting of at least said first imaging optics system or said at least one second imaging optics system.

15. The medical imaging apparatus as claimed in claim 4, wherein said first imaging optics system and said second imaging optics system are associated with a first field of view and a second field of view inside said patient receiving zone, respectively, the first field of view being associated with a region that includes an isocenter of the medical imaging apparatus in which a body region of a patient to be examined is arranged for the purpose of the medical imaging examination.

16. The medical imaging apparatus as claimed in claim 1, wherein the at least one positional data acquisition unit is arranged in a central region of the patient receiving zone.

17. The medical imaging apparatus of claim 1, wherein said first imaging optics system covers a larger portion of an image acquisition aperture associated with the camera and/or of the lens surface of the camera associated with the at least one positional data acquisition unit than the second imaging optics system.

18. The medical imaging apparatus of claim 1, wherein said first imaging optics system and said second imaging optics system cover respectively different lens surfaces of the camera associated with the at least one positional data acquisition unit.

* * * * *